United States Patent [19]

Shannon, Sr.

[11] 4,067,327
[45] Jan. 10, 1978

[54] TABBED TOWEL

[76] Inventor: A. Vernon Shannon, Sr., 19 Greenhouse Drive, Princeton, N.J. 08540

[21] Appl. No.: 722,980

[22] Filed: Sept. 13, 1976

[51] Int. Cl.$^2$ ............................................. A61F 13/00
[52] U.S. Cl. ................................................. 128/132 D
[58] Field of Search ............... 128/132 D, 132 R, 292, 128/296

[56] References Cited

U.S. PATENT DOCUMENTS

| | | | |
|---|---|---|---|
| 3,263,680 | 8/1966 | Morgan | 128/132 D |
| 3,889,667 | 6/1975 | Collins | 128/132 D |
| 3,916,887 | 11/1975 | Kelly | 128/132 D |
| 3,930,497 | 1/1976 | Krebs et al. | 128/132 D |

Primary Examiner—Lawrence W. Trapp
Attorney, Agent, or Firm—Behr & Woodbridge

[57] ABSTRACT

A tabbed surgical towel includes a double-backed adhesive layer, a release layer attached thereto and a pair of tabs located between the release layer and the adhesive layer and situated at opposite extreme edges of the towel. The release layer and the double-backed adhesive layer preferably comprise elongated strips of material which extend across the width of the rectangular towel. Each tab is substantially as wide as the release layer and the adhesive layer and does not extend beyond either layer such that the tab is substantially hidden by the release layer when the release layer is pressed against the adhesive layer at both ends thereof. Generally the tab is considerably shorter than the adhesive release layer and would be approximately ¾ inch in length according to the preferred embodiment. It has been found that a tab having approximately the same dimensions as the release and the adhesive layers allows the user of the towel to readily obtain a purchase on the release layer without inadvertently pulling up a portion of the underlying adhesive layer.

8 Claims, 4 Drawing Figures

TABBED TOWEL

CROSS-REFERENCE TO RELATED APPLICATIONS

This invention may be manufactured according to the method and apparatus disclosed in a copending U.S. patent application entitled "Towel Tabbing Machine" by Frank Baumgartner.

BACKGROUND OF THE INVENTION

1. Field of the Invention

This invention relates to a surgical towel or drape having an improved tab structure.

2. Description of the Prior Art

The use of adhesive strips on surgical towels is known to those of ordinary skill in the art. For example, Kelly, U.S. Pat. No. 3,916,887 discloses a "Surgical Drape with Adhesive on Top and Bottom" wherein the drape includes a tab located between an adhesive layer and a release layer. Kelly's invention, however, is fundamentally different from the towel of the present invention in that the tab is very long and runs the width of the drape. Other towels of interest are disclosed in the following patents: Hoff, U.S. Pat. No. 3,470,590; Mesek et al., U.S. Pat. No. 3,840,013; Krebbs et al., U.S. Pat. No. 3,930,497; Karami, U.S. Pat. No. 3,893,460; and Melges, U.S. Pat. No. 3,494,356.

Towels similar in structure to that of the present invention were previously made by hand. Tabs comprising small address-type labels were inserted manually between the release layer and one side of the double-backed adhesive tape layer. There are several disadvantages to this prior art method. First of all, being manual the method was labor intensive and therefore expensive. Second of all, the tab frequently overlapped the adhesive layer thereby consuming more tab stock than necessary. Thirdly, the registration between the tab and the adhesive tape layer was not as good as could be achieved by automated methods.

There are some machines known in the prior art which will insert a first material between two layers of a second material. For example, Wang, U.S. Pat. No. 2,995,174 discloses a method of inserting a clip between two layers of bag material. Van Cleff, U.S. Pat. No. 2,248,318 and Beck, U.S. Pat. No. 3,298,891 also disclose prior art machinery of interest. However, none of the prior art appears to disclose an automatic method for inserting a tab between the release layer and the adhesive layer of adhesive tape stock. In particular, none of the prior art appears to disclose a surgical drape or towel having tabs of the same proportions and materials as described in the present invention nor does the prior art appear to disclose an apparatus or method which would be suitable for making said tabbed towel.

SUMMARY OF THE INVENTION

Briefly described, the present invention comprises a surgical towel or drape having a double-backed adhesive strip layer, a release layer strip attached thereto and a pair of release tabs sandwiched between the adhesive strip layer and the release strip layer and located at opposite ends thereof. The tabs are approximately ¾ inch long × ½ inch wide. Both the adhesive strip layer and the release strip layer are approximately 26 inches long by ½ inch wide. When correctly in position, both tabs substantially completely cover the first ¾ inch of the adhesive layer without any significant overlap. Therefore the last ¾ inch of release layer material does not adhere to the adhesive strip layer and accordingly can be readily gripped by the fingers and removed. The fact that the tab does not extend beyond the sides or end of the adhesive layer makes it very unlikely that the tab can be inadvertently picked up and the adhesive layer along with it. Conversely, since that tab is no shorter than the width of the adhesive layer, it is highly unlikely that the adhesive layer can be inadvertently picked up and at least partially disengaged from the towel. The dimensioning of the tab relative to the adhesive and the release layer is an important factor of the present invention. These and other features of the present invention will be more fully understood with reference to the following drawings and detailed description of the invention.

BRIEF DESCRIPTION OF THE DRAWINGS

FIG. 2b is a detailed view of one of the tab sections of the towel illustrated in FIG. 2a.

DETAILED DESCRIPTION OF THE INVENTION

During the course of this description like numbers will be used to designate like elements according to the different figures illustrating the invention.

Figure 1:
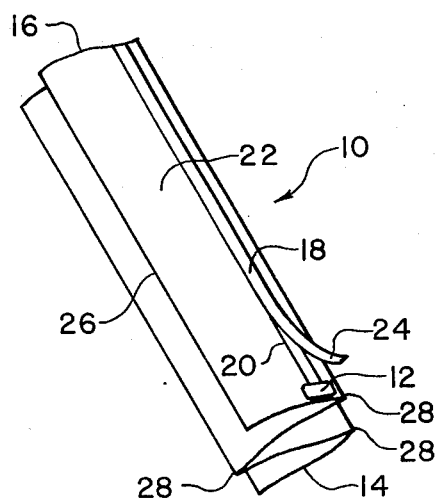
FIG. 1 is a perspective view of a prior art towel having manually attached tabs.

FIG. 1 illustrates a prior art towel 10 which includes a manually attached tab 12 at the leading edge 14 of the towel. There is no tab at the trailing edge 16 of the towel. The tab 12 covers the leading edge of a double-backed adhesive layer 20. Adhesive layer 20 has adhesive on both sides such that it will stick to the towel stock 22. A backing release paper 18 also sticks to the adhesive layer 20, but with very little force. Accordingly, the release layer 18 can be easily stripped away from the double adhesive layer 22. The towel can then be attached to the object which it is meant to cover. Typically, such a towel is used to cover a patient during a surgical operation and also serves as a clean field upon which the surgeon may operate. The tab 12 is located adjacent to the leading edge 14 and directly between the lower adhesive layer and the top release layer 18. The tab 12 sticks to the lower adhesive layer 20 but does not adhere to the upper release layer 18. Therefore, a small leading portion 24 of the upper release layer 18 always projects above the plane of the towel 22. It is relatively easy for the user of the towel to grab the release layer 18 by the front portion 22 and strip the release layer 18 away from the adhesive backing 20. This renders the towel readily usable for its purpose as a surgical drape or the like. According to the prior art and also according to the preferred embodiment of the present invention the adhesive layer 20 and the release layer 18 run in a direction parallel to the side edge 26 of the towel. It therefore follows that the adhesive layer 20 and the release layer 18 also run in a direction parallel to the longitudinal folds 28 of the towel.

The prior art towel just described has several major disadvantages when compared to the towel of the present invention. Since the tabbing of the prior art towel is a manual operation, such towels can be very expensive and time consuming to manufacture. Since they are time consuming it is generally only economical to place one tab 12 at the leading edge. This can be inconvenient since the user may have to inspect both ends of the towel before finding the tab 12. One major difficulty experienced with the prior art tab 12 that it significantly overlaps the lower adhesive layer 20. In other words, the tab 12 may be as much as ⅛ inch to ¼ inch wider than the adhesive layer 20 or the release layer 18. This is undesirable since it would not be difficult for a user to grab the tab 12 accidentally and inadvertently rip off the adhesive layer 20. Prior art tabs 12 typically comprise a label-like stock having adhesive on the underside. If the tab 12 were not squarely situated on the towel 22 but were allowed to extend beyond the leading edge 14 then it was found that the tab 12 would stick to other undesired portions of the towel or to other towels. These and other problems with the prior art towels were overcome by the structure illustrated in FIGS. 2a–2c.

Figure 2A:
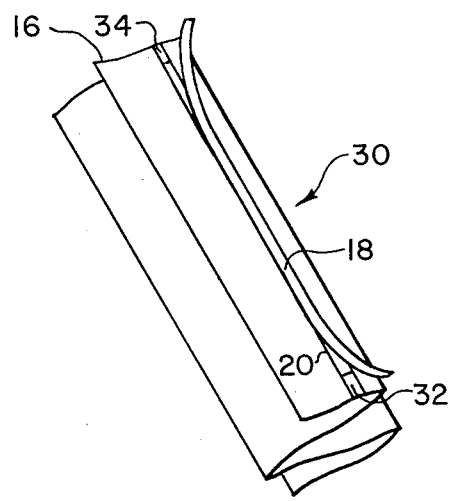
FIG. 2a is a perspective view of the towel of the present invention according to a preferred embodiment thereof.

A folded towel 30 according to the present invention is illustrated in FIG. 2a. Those features that towel 30 has in common with prior art towel 10 are given similar numbers. Towel 30 is like prior art towel 10 in that there is a leading edge tab 32 between the release layer 18 and the adhesive layer 20. In addition, there is a trailing edge tab 34 located at the trailing edge 16 of the towel 30.

Figure 2B:
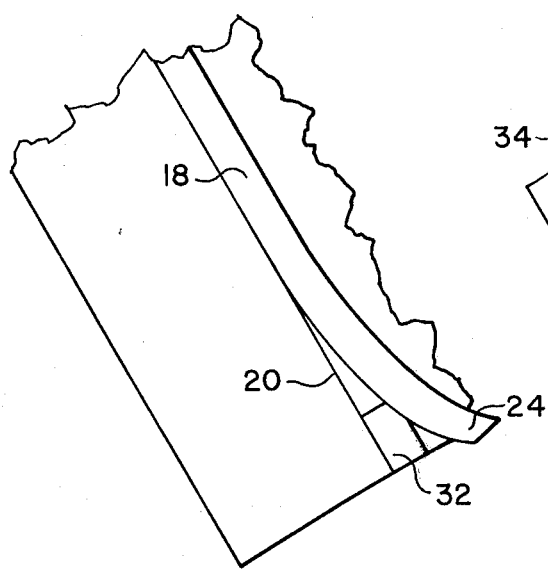

A detail of the leading edge tab 32 is illustrated in FIG. 2b. The tab 32 differs from prior art tab 12 in that it does not significantly extend beyond the sides of the lower adhesive layer 20 or the release layer 18. On the other hand, the width of the leading edge tab 32 is not significantly less than the width of the lower adhesive tape 20 or the top release layer 18. The tab 32 cannot be significantly less than the width of the lower adhesive layer 20, otherwise it loses part of its function as a tab. On the other hand, it cannot be significantly wider than the lower adhesive layer 20 because of the difficulty encountered with wide tabs such as those described as element 12 in the prior art towel 10.

Figure 2C:
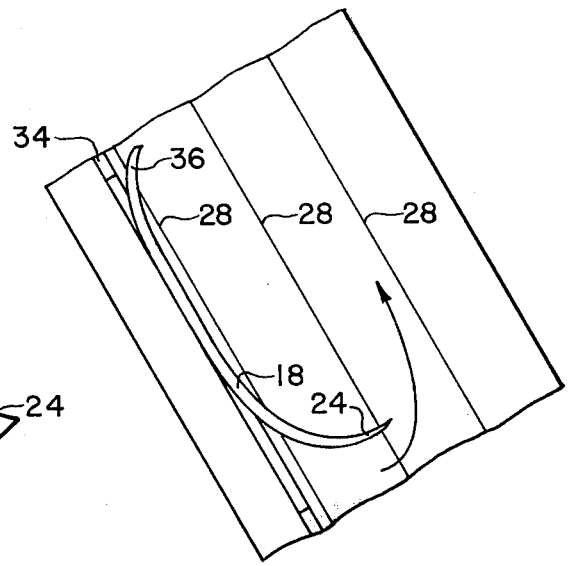
FIG. 2c illustrates the manner in which the release layer is separated from the adhesive layer when attached to a towel.

Towel 30 is prepared for use by grabbing the leading edge 24 and stripping off the release layer 18 in the manner illustrated in FIG. 2c. The stripping operation can be performed in reverse by grabbing the trailing edge 36 of the release layer 18 and pulling the release layer 18 in the opposite direction.

There are several major advantages to the towel just described. First of all, the release layer may be readily separated from the adhesive layer of the towel without damaging the towel by inadvertently ripping up the adhesive strip layer. This of course results in greater economies and efficiencies to the towel user. Second of all, there are efficiencies gained and costs saved in tabbing materials since only as much tabbing material is used as is necessary to perform the function. Due to the inaccuracies of the prior art manual method of attaching tabs it was necessary to use tabs considerably wider than functionally required in order to compensate for human error. Typically, sticky backed small address-type labels were used. Stickiness was necessary so that the portion of the tab which overlapped the tape did not stick up in the air but rather attached itself to the towel stock. Unfortunately, it was found that the tab would sometimes stick up in the air and would inadvertently cause the adhesive layer to be ripped up along with the release layer. Considerable tab stock economies were achieved by going from individually precut sticky backed address-type labels to a less expensive label stock. Thirdly, the above-described towel structure lent itself nicely to manufacture by automatic methods and apparatus. At the request of the inventor, Mr. Frank Baumgartner invented a machine and automatic method which would produce the towels which are the subject of this present invention. A complete description of the Baumgartner apparatus and method can be found in his copending application entitled "Towel Tabbing Machine". The automating of the tabbing procedure has, of course, resulted in additional economies.

It will be appreciated by those of ordinary skill in the art that various modifications can be made to the basic invention. According to the preferred embodiment the towel measures approximately 17 inches wide and 26 inches long. Accordingly, the release layer and the adhesive layer are likewise 26 inches long and both measure ½ inch wide. The tabs extend inwardly from each edge of the towel a distance of approximately ¾ inch. The tabs may be as short as ⅜ inch or less or could be longer than ¾ inch, depending upon the particular desired requirements. However, as previously discussed, the tab must substantially cover all of the first ¾ inch of the adhesive tape at both ends without significantly extending beyond the edges of the adhesive layer.

The term double-backed adhesive tape or double-sticky backed tape has been used to describe a commercially available tape which includes a release layer 18 and a double sided adhesive layer 20. The same type of tape is also referred to in the trade as double-faced tape.

While the invention has been described with reference to a preferred embodiment thereof, it will be appreciated by those of ordinary skill in the art that various different changes and modifications can be made to the invention and the parts thereof without departing from the spirit and scope of the invention.

I claim:
1. A tabbed towel comprising:
 a towel having at least a first and a second edge;
 an adhesive layer attached to said towel and extending from said first edge to said second edge, said adhesive layer having a predetermined width, less than the width of said towel;
 a release layer attached to said adhesive layer extending from said first edge to said second edge, said release layer having substantially the same width as said adhesive layer;
 a first tab located between said adhesive layer and said release layer, said tab having a length less than the length of either the adhesive layer and said release layer and a width substantially the same as said release layer and said adhesive layer, said tab being at the first edge of said towel; and,
 a second tab located between said adhesive layer and said release layer, said second tab havng a length less than the length of either the adhesive layer and said release layer and a width substantially the same as said release layer and said adhesive layer, said second tab being at the second edge of said towel.

2. The tabbed towel of claim 1 wherein said adhesive layer and said release layer comprise strips having a width in the range of ¼ inch to 2 inches.

3. The tabbed towel of claim 2 wherein the width of said adhesive layer and said release layer is approximately ½ inch.

4. The apparatus of claim 3 wherein the distance from said first edge to said second edge is approximately 26 inches.

5. The apparatus of claim 4 wherein said towel comprises a surgical drape.

6. The tabbed towel of claim 5 wherein said adhesive layer has adhesive on both sides thereof.

7. The tabbed towel of claim 6 wherein said first and second tabs are approximately ½ inch to ¾ inch in length and approximately ½ inch in width.

8. The tabbed towel of claim 7 wherein said first and second tabs do not substantially extend beyond the edges of said adhesive layer.

* * * * *